(12) United States Patent
Nexø et al.

(10) Patent No.: US 7,727,972 B2
(45) Date of Patent: Jun. 1, 2010

(54) METHODS FOR DETERMINING ABSORPTION OF COBALAMIN OR ANALOGUES THEREOF

(75) Inventors: Ebba Nexø, Åbyhøj (DK); Anne Louise Mørkbak, Hinnerup (DK)

(73) Assignee: DrugTech Corporation, Wilmington, DE (US)

( * ) Notice: Subject to any disclaimer, the term of this patent is extended or adjusted under 35 U.S.C. 154(b) by 577 days.

(21) Appl. No.: 11/658,774

(22) PCT Filed: Jul. 29, 2005

(86) PCT No.: PCT/DK2005/000512

§ 371 (c)(1),
(2), (4) Date: Jan. 29, 2007

(87) PCT Pub. No.: WO2006/010369

PCT Pub. Date: Feb. 2, 2006

(65) Prior Publication Data

US 2009/0162882 A1    Jun. 25, 2009

(30) Foreign Application Priority Data

Jul. 29, 2004    (DK) .............................. 2004 01159

(51) Int. Cl.
    *A61K 31/70*    (2006.01)
(52) U.S. Cl. ....................... 514/52; 536/26.4
(58) Field of Classification Search ............ 514/52; 536/26.4
    See application file for complete search history.

(56) References Cited

U.S. PATENT DOCUMENTS

| | | | |
|---|---|---|---|
| 3,981,863 A | 9/1976 | Niswender et al. ............ 536/25 |
| 5,506,109 A | 4/1996 | Pourfarzaneh et al. ...... 435/7.92 |
| 2004/0268440 A1 | 12/2004 | Berglund et al. ............ 800/288 |
| 2006/0166271 A1* | 7/2006 | Berglund et al. ............. 435/7.1 |

FOREIGN PATENT DOCUMENTS

WO    WO 2006010369    2/2006

OTHER PUBLICATIONS

Burger et al., "Human Plasma R-Type Vitamin $B_{12}$-binding Proteins. I. Isolation and Characterization of Transcobalamin I, Transcobalamin III, and the Normal Granulocyte Vitamin$_{B12}$-Binding Protein," *J. Biol. Chem.*, 250(19):7700-7706, Oct. 10, 1975.

Carmel, "Vitamin $B_{12}$-binding Proteins in Serum and Plasma in Various Disorders. Effect of Anticoagulants," *Am. J. Clin. Pathol.*, 69:317-25, 1978.

Carmel, "R-Binder Deficiency. A Clinically Benign Cause of Cobalamin Pseudodeficiency," *JAMA*, 250(14):1886-90, Oct. 14, 1983.

Carmel et al., "Plasma Total Transcobalamin I. Ethnic/Racial Patterns and Comparison With Lactoferrin," *Am. J. Clin. Pathol.*, 116:576-80, 2001.

Carmel, "Mild Transcobalamin I (Haptocorrin) Deficiency and Low Serum Cobalamin Concentrations," *Clin. Chem.*, 49(8):1367-74, 2003.

Gimsing et al., "Increased Concentration of Transcobalamin I in a Patient with Metastatic Carcinoma of the Breast," *Scand. J. Haematol.*, 21:243-49, 1978.

Hall et al., "Improved Method for the Extraction of Vitamin $B_{12}$ from Serum," *J. Lab. Clin. Med.* 63(3):517-23, Mar. 1964.

Jørgensen et al., "An Immunoassay Designed to Quantitate Different Molecular Forms of Rat Urinary Epidermal Growth Factor with Equimolar Potency: Application on Fresh Rat Urine," *Scand. J. Clin. Lab. Invest.*, 56:25-36, 1996.

Lindemans et al., "Application of a Simple Immunoadsorption Assay for the Measurement of Saturated and Unsaturated Transcobalamin II and R-binders," *Clin. Chim. Acta*, 132:53-61, 1983.

Lindgren et al., "Holotranscobalamin—a Sensitive Marker of Cobalamin Malabsorption," *Eur. J. Clin. Invest.*, 29:321-29, 1999.

Morelli et al., "A Radioimmunoassay for the R-Type Binders of Cobalamin," *Clin. Chim. Acta*, 77:365-72, 1977.

Nexø et al., "Characterization of a Cobalamin-binding Plasma Protein from a Patient with Hepatoma," *Scand. J. Clin. Lab. Invest.*, 35:683-90, 1975.

(Continued)

*Primary Examiner*—Ralph Gitomer (57) ABSTRACT

The present invention relates to a method for determining absorption of cobalamin or analogues thereof in an individual comprising (ii providing two blood samples from said individual, wherein the first sample comprises said individual's blood prior to ingestion by said individual of non-radioactive cobalamin or an analogue thereof and the second sample comprises said individual's blood after said ingestion, (ii) determining the concentration of cobalamin or analogue thereof in the first sample, (iii) determining the concentration of cobalamin or analogue thereof in the second sample by treating complexes of cobalamin or analogue thereof and one or more carrier proteins with one or more enzymes to release cobalamin or analogue thereof from said one or more carrier proteins, and (iv) determining, on the basis of comparison of said concentrations in said two samples, whether said cobalamin or analogue thereof has been absorbed in the blood stream.

3 Claims, 5 Drawing Sheets

OTHER PUBLICATIONS

Nexø, "A New Principle in Biospecific Affinity Chromatography Used for Purification of Cobalamin-binding Proteins," *Biochim. Biophys. Acta.*, 379:189-92, 1975.

Nexø et al., "A Rare Case of Megaloblastic Anaemia Caused by Disturbances in the Plasma Cobalamin Binding Proteins in a Patient with Hepatocellular Carcinoma," *Scand. J. Haematol.*, 14:320-27, 1975.

Nexø, "Transcobalamin I and other Human R-binders: Purification, Structural, Spectral and Physiological Studies," FADL's forlag, Copenhagen, 1978.

Nexø, "Cobalamin Binding Proteins," In: Kräutler, B. et al. (Eds.), "Vitamin $B_{12}$ and $B_{12}$- Proteins," Wiley-VCH, 1998.

Nexø et al., "Measurement of Transcobalamin by ELISA," *Clin. Chem.*, 46(10):1643-49, 2000.

Raven et al., "Extraction of Serum Vitamin $B_{12}$ for Radio-isotopic and *Lactobacillus leischmannii* Assay,"*J. Clin. Path.*, 28:531-39, 1975.

Sandberg et al., "The Content, Binding, and Forms of Vitamin $B_{12}$ in Milk[1-3]," *Am. J. Clin. Nutrition*, 34:1717-24, Sep. 1981.

Stenman, "Characterization of R-Type Vitamin $B_{12}$-Binding Proteins by Isoelectric Focusing II. Comparison of Cobalophilin (R Proteins) From Different Sources," *Scand. J. Clin. Lab. Invest.*, 35:147-55, 1975.

Ulleland et al., "Direct Assay for Cobalamin Bound to Transcobalamin (Holo-transcobalamin) in Serum," *Clin. Chem.*, 48(3):526-32, 2002.

Yang et al., "The Biochemical and Genetic Basis for the Microheterogeneity of Human R-Type Vitamin $B_{12}$ Binding Proteins," *Blood*, 59(4):747-55, Apr. 1982.

Zelder et al., "On the Role of Two Different Cobalt (II) Species in Coenzyme $B_{12}$-Dependent 2-Methylenegluterate Mutase from *Clostridium barkeri*," *Biol. Chem. Hoppe-Seyler*, 374:85-90, Jan. 1993.

Loikas et al., Blood, vol. 98, No. 11, part 2, pp. 6B -Abstract (2001).

Rothenberg et al., Journal of Laboratory and Clinical Medicine, vol. 103, No. 6, pp. 959-972 (1984).

Ulleland M. et al., Direct Assay for Cobalamin Bound to Transcobalami N (HoloTranscobalami N) I N Serum, Clinical Chemistry, American Association for Clinical Chemistry, Washington, DC, us, vol. 48, No. 3, Mar. (2002).

Zelder O., et al., On the Role of Two Different Cobalt (II) Species in Coenzyme B-12-dependent 2-methyl enegl utarate mutase from *Clostridium barkeri*, Biological Chemistry Hoppe-Seyler, vol. 374, No. 1, pp. 85-90, (1993).

Office Action, dated Dec. 5, 2008 issued in U.S. Appl. No. 10/549,077.

International Search Report, PCT/DK2005/000512 published in WO 2006/010369 A3 dated Feb. 2, 2006.

* cited by examiner

METHODS FOR DETERMINING ABSORPTION OF COBALAMIN OR ANALOGUES THEREOF

All patent and non-patent references cited in the present application are hereby incorporated by reference in their entirety.

FIELD OF THE INVENTION

The present invention relates to methods for the quantification of proteins and of non-proteinaceous protein-bound compounds in samples, in particular the quantification of cobalamin (vitamin B12) and cobalamin-binding proteins, such as haptocorrin. The methods of the invention comprise enzymatic modification of such proteins in order to liberate or release their non-proteinaceous ligands and/or to facilitate protein detection. Examples of these modifications include deglycosylation and proteolytic degradation.

BACKGROUND OF THE INVENTION

In nature, many non-proteinaceous compounds, such as vitamins and hormones, occur mostly in a form complexed, i.e. bound, to proteins. Detection and quantification of such bound non-proteinaceous compounds is often difficult due to insufficient accessibility. In many instances, liberation or release of the non-proteinaceous compound from the protein to which it is bound will be necessary to allow detection. Many known methods of liberating non-proteinaceous compounds from complexes with proteins result in undesired modification of the non-proteinaceous compound.

An example of such a non-proteinaceous compound is cobalamin, which, in the blood stream, can be bound to two cobalamin-binding proteins; transcobalamin (TC) and haptocorrin (HC). Cobalamin is an essential vitamin, which in man is necessary for cell proliferation and metabolism. Patients suffering from cobalamin deficiency are at risk of developing nerve damage, with typical symptoms of reduced sensitivity in hands and feet and memory loss. Cobalamin deficiency is a public health problem affecting the elderly in particular. Approximately 5-20% of the elderly population is affected. There is an outspoken medical need for diagnostic methods allowing early identification of persons at risk of developing deficiency, as this damage may become irreversible of not treated in the early stages. A consequence of cobalamin deficiency that has come into focus in recent years is that it results in increased blood concentrations of homocysteine, an independent risk factor for cardiovascular disease.

Measurement of cobalamin is only possible after release from the proteins. Prior art methods for the release of cobalamin from a binding protein generally use base extraction. E.g. in a HoloTC RIA assay available from Axis-Shield Biochemicals, cobalamin is released from TC using dithiothreitol and sodium hydroxide. U.S. Pat. No. 4,300,907 describes release using acetone, reducing agent and cyanide ions. These extraction methods often result in a modification of the cobalamin molecules. Furthermore, they result in a pH level which is unfavourable for further analysis.

Thus, there is a need for simple and improved methods of quantifying protein-bound non-proteinaceous compounds, in particular protein-bound cobalamin and analogues thereof.

For the diagnosis of cobalamin deficiency, it is important to know whether absorption of cobalamin from the food is impaired. The transfer of cobalamin from the food to the blood involves intrinsic factor. Intrinsic factor binds to cobalamin in the intestine and the intrinsic factor-cobalamin complex is later absorbed by epithelial cells in the terminal ileum through binding to a receptor, cubilin. In the epithelial cell, cobalamin is separated from intrinsic factor and transferred to the blood, where it binds to transcobalamin and haptocorrin present in plasma.

In many patients, cobalamin deficiency is caused by no or reduced secretion of intrinsic factor into the gastric juice. Ingestion of both intrinsic factor and cobalamin by these patients will cause a significant increase in the absorption of cobalamin. The fact that absorption of cobalamin to the blood can be restored in patients with no intrinsic factor secretion simply by adding cobalamin together with intrinsic factor is used in a routine test, the Schilling test, employed in patient diagnosis of cobalamin deficiency (Ward (2002) Clin. Lab. Med. 22:435-445). The aim is to determine whether the patient has a reduced secretion of intrinsic factor or an intestinal malabsorption of cobalamin. The classical version of the Schilling test consists of two steps. In the first part, free radioactive cobalamin is ingested by the patient after having received an injection of a huge dose of unlabelled (non-radioactive) cobalamin in order to saturate cobalamin-binding proteins. This ensures that any absorbed labelled cobalamin is excreted in the urine. Urine is then collected over the next 24 hours and the amount of radioactive cobalamin present is determined. If very little radioactivity is present in the urine, this indicates a lack of cobalamin absorption which may be caused by an intrinsic factor deficiency, such as a lack of intrinsic factor secretion, or by intestinal malabsorption. To distinguish between these two conditions the second part of the Schilling test is performed. In this part of the test, the patient ingests radioactive cobalamin together with intrinsic factor. Again the urine is collected over the next 24 hours and the radioactivity determined. A significant increase of radioactivity in the urine supports the diagnosis that the patient suffers from a lack of intrinsic factor, since the cobalamin absorption was restored by ingestion of cobalamin together with intrinsic factor. No radioactivity in the urine indicates that the patient has a defect further along the process of cobalamin absorption e.g. a malfunction of the intestine.

The Schilling test has been marketed in several modifications. One is to supply the labelled cobalamin built into food rather than in its free form. This has been done in order to test whether the patients' inability to absorb relates to a decreased capacity in liberating the cobalamin from food, such as it may be seen in patients suffering from pancreatic insufficiency.

Whatever the format of the Schilling test there are several severe problems and limitations attached to this method:

Most important is the use of labelled cobalamin. Though the amount of radioactivity employed is limited (magnitude $0.5 \times 10^{-6}$ ci) it is increasingly unacceptable both for the patient and for the clinical personnel handling the radioactive cobalamin and collecting the biological material needed for the test.

The collection of urine over a 24 hour period is problematic. It is time consuming and it is hampered by a relatively large uncertainty due to incomplete collection of the urine from the patient.

Thus, there is a need for alternatives to the Schilling test which do not use radioactivity.

Determination of the cobalamin status of an individual often also requires determination of the levels of the free (apo) and/or bound (holo) form of cobalamin-binding proteins, such as transcobalamin or haptocorrin. Haptocorrin is a glycoprotein. Reliable measurement of the total level of glycoproteins in a sample requires that different species or isoforms of the glycoprotein present react alike in the assay to be used. This represents a problem when measuring heavily glycosylated proteins such as haptocorrin. Haptocorrin is present in plasma and in a number of other body fluids. Haptocorrin molecules from various sources differ in their glycosylation pattern. Furthermore, the glycosylation of plasma haptocorrin may differ amongst patients (1, 2, 3, 4, 5). Plasma haptocorrin carries 70% of the circulating cobalamin, however, the role in cobalamin transport and metabolism is still unclear. In addition to its role in cobalamin storage in the bloodstream, the protein was proven of clinical interest in connection with conditions where the protein is observed in an increased concentration, such as chronic myeloid leukaemia, polycythaemia vera, acute leukaemia, leukocytosis, cancer and hepatic disease (6, 7). Thus, haptocorrin may be interesting as a marker protein for these diseases. Recently, it has further been suggested that a low plasma concentration of cobalamin might be caused by heterozygosity for lack of this protein (8), and thereby that measurement of haptocorrin may be of help when interpreting a low level of plasma cobalamin.

Two radioimmunoassays for direct measurement of total haptocorrin have been described (9, 10, 11). However, the influence of the heterogeneous glycosylation of haptocorrin on its measurement in different plasma samples has not been investigated, and it is thus unclear whether these assays measure haptocorrin in various samples on an equimolar base.

The present invention in one aspect relates to a method for quantifying glycoproteins comprising a step of removal of glycosylation before quantification. Enzymatic deglycosylation of glycoproteins can have very different consequences for antibody-based detection of such proteins depending, e.g. on the effect of glycosylation on the accessibility of the polypeptide chain. While deglycosylation of granulocyte/macrophage colony-stimulating factor increased immunoreactivity 4 to 8 fold (Moonen et al. (1987) Proc. Natl. Acad. Sci. USA 84:4428-4431), deglycosylation of human thyroid peroxidase resulted in no or only slightly enhanced detection (Giraud et al. (1992) J. Endocrinol. 132:317-323). Thus, the effect of deglycosylation of glycoproteins on their immunoreactivity is highly unpredictable. For proteins that only exhibit limited or no heterogeneity in their carbohydrate chains, this may not be of much practical importance. However, for heterogeneously-glycosylated marker proteins, such as haptocorrin, an glycosylation-independent detection method is of great importance for accurate analysis of samples and diagnosis of disease.

SUMMARY OF THE INVENTION

It can be concluded from the above that there is a need for improved methods for the detection of non-proteinaceous compounds that are bound to proteins. For example, there is a need for improved methods for detection of protein-bound cobalamin and analogues thereof.

In a first main aspect, the invention relates to a method for quantifying a non-proteinaceous compound bound to one or more carrier proteins in a sample comprising the steps of:
  i) separating complexes of said non-proteinaceous compound bound to said one or more carrier proteins from the non-proteinaceous compound that is not bound to said one or more carrier proteins;
  ii) releasing the non-proteinaceous compound from said one or more carrier proteins by treating the complexes of (i) with one or more enzymes;
  iii) quantifying the non-proteinaceous compound enzymatically released in step (ii).

Release of non-proteinaceous compounds from a complex using enzymes rather than e.g. denaturing chemicals has several advantages.

Firstly, the treatment does not result in modification of the non-proteinaceous compound to be assayed. In particular for cobalamin and analogues thereof, but also for other compounds, it is important to avoid such modification, since depending on the method of detection, modified forms may escape detection and thus, modifications may result in an underestimation of the amount of cobalamin or analogue thereof. For instance, modification of the corrin-structure due to acid/base treatment may result in reduced binding to transcobalamin or intrinsic factor, in particular intrinsic factor. This is a problem if these proteins are used as catching proteins in the quantification step.

Furthermore, importantly, it is often of interest to perform, on a blood sample from a patient, a qualitative or quantitative analysis of the spectrum of cobalamin and analogues thereof bound to transcobalamin and/or haptocorrin. For example, since many analogues of cobalamin are not biologically active in humans, it is often of interest to be able to determine whether, and to which extent, the compounds bound to transcobalamin and/or haptocorrin are cobalamin or whether, and to which extent, they are analogues of cobalamin. This determination is more complicated, or even impossible, if modification occurs during release from the proteins. The method of the present invention, which does not modify the cobalamin or analogues thereof during release, renders such a further analysis easier.

Moreover, using the enzymatic method of the invention, the non-proteinaceous compound is released in conditions that often are suitable for further analysis, for further purification or for further modifications. Extreme pH values, for instance, can be avoided. Furthermore, enzymatic treatment is relatively fast and inexpensive.

The above described method of the invention for improved detection of non-proteinaceous compounds bound to proteins using enzymatic release, allows detection of cobalamin and analogues thereof bound to proteins in blood samples. This has made it possible to design an alternative Schilling test.

Thus, in a further main aspect, the invention relates to a method for determining absorption of cobalamin or an analogue thereof in an individual comprising the steps of:
  i) providing two blood samples from said individual, wherein the first sample was taken before ingestion by said individual of non-radioactive cobalamin or an analogue thereof, together with binding protein or without a binding protein, and the second sample was taken after said ingestion,
  ii) determining the concentration of cobalamin or analogue thereof in said samples using any of the quantification methods described herein, and
  iii) determining, on the basis of comparison of said concentrations in said two samples, whether said cobalamin or analogue thereof has been absorbed in the blood stream.

The cause of a cobalamin-related deficiency in a patient can be more precisely diagnosed by performing the above method two times, once with samples taken before and after ingestion of cobalamin or analogue thereof alone and once with samples taken before and after ingestion of cobalamin or analogue thereof with a binding protein, such as intrinsic factor. An increased presence of cobalamin or analogue thereof in blood samples taken after ingestion together with a binding protein is indicative of the deficiency being related to insufficient intrinsic factor. The use of radioactive cobalamin is herewith avoided.

In addition, as explained above, there is a need for improved detection of glycoproteins, such as glycosylated cobalamin-binding proteins, e.g. haptocorrin.

In a further main aspect, the invention relates to a method for quantifying a glycoprotein in a sample comprising the steps of:
i) treating a sample with deglycosylating enzyme; and
ii) quantifying said glycoprotein.

The method solves problems related to accurate quantification of glycoproteins, in particular heavily-glycosylated and heterogeneously-glycosylated proteins.

In a preferred embodiment, the glycoprotein is a cobalamin-binding protein. The above method for quantification of glycoproteins, in particular haptocorrin, provides the advantage that it is sensitive and independent of the degree of glycosylation of the protein, thus providing a more accurate determination of the molar concentration of such proteins in samples.

DESCRIPTION OF THE DRAWINGS

● Tris HCl; ◆ Proteinase K (50 U); ■ Subtilisin (25 U); ◇ Extractant; ▲ Blind.

DETAILED DESCRIPTION OF THE INVENTION

Definitions

Carrier protein—protein capable of forming a complex with a non-proteinaceous compound.

Catching protein—protein capable of binding a non-proteinaceous compound used in the detection of said compound.

Deglycosylating enzyme—enzyme capable of at least partially removing carbohydrates from glycoproteins.

Indicator moiety—compound used for the detection and quantification of a protein of interest, including antibodies and fragments or other equivalents thereof.

Non-proteinaceous compound—compound that is not a protein or a peptide.

Cobalamin and analogues thereof—when used herein, the term "cobalamin" or "vitamin B12" includes all subspecies of cobalamin having different beta groups, such as, but not limited to, cyanocobalamin, hydroxycobalamin, methylcobalamin, and adenosylcobalamin. Analogues of cobalamin, when used herein, include all corrinoids other than cobalamin. Preferred analogues of cobalamin are analogues capable of binding to cobalamin-binding proteins, more preferably analogues capable of binding to any one or more of: transcobalamin, haptocorrin, and intrinsic factor. Most preferred are analogues capable of binding transcobalamin and/or haptocorrin.

Small organic compounds—refers herein to non-oligomeric, carbon containing compounds having a size of less than 20000 daltons, preferably a small organic compound of less than 10000 daltons, more preferably less than 5000 daltons, most preferably less than 2000 daltons.

Methods of Quantifying Non-Proteinaceous Compounds

In a first main aspect, the invention relates to a method for quantifying a non-proteinaceous compound bound to one or more carrier proteins in a sample comprising the steps of:
i) separating complexes of said non-proteinaceous compound bound to said one or more carrier proteins from molecules of the non-proteinaceous compound that are not bound to said one or more carrier proteins;
ii) releasing the non-proteinaceous compound from said one or more carrier proteins by treating the complexes of (i) with one or more enzymes;
iii) quantifying the non-proteinaceous compound enzymatically released in step (ii).

Thus, using the above method, the amount and/or concentration of a non-proteinaceous compound bound to a carrier protein in said sample can be determined.

In a preferred embodiment of the above method, said non-proteinaceous compound does not contain a single peptide bond.

In another preferred embodiment, said non-proteinaceous compounds is a small organic compound, preferably a small organic compound of less than 10000 daltons, more preferably less than 5000 daltons, most preferably less than 2000 daltons.

In other preferred embodiments, said non-proteinaceous compound is a small organic compound of less than 20000 daltons but more than 100 daltons, such as a small organic compound of less than 5000 daltons but more than 500 daltons.

In another preferred embodiment, said non-proteinaceous compound is not a nucleic acid.

In another preferred embodiment, said non-proteinaceous compound is a vitamin, preferably cobalamin (vitamin B12), vitamin A or vitamin D, or an analogue of any of these.

In a more preferred embodiment, said non-proteinaceous compound is cobalamin, a subspecies of cobalamin, an analogue of cobalamin or a mixture of cobalamins and/or analogues thereof.

Thus, in one highly preferred embodiment, said non-proteinaceous compound is cobalamin, a subspecies of cobalamin, or an analogue of cobalamin. Preferred subspecies of cobalamin are cyanocobalamin, hydroxycobalamin, methylcobalamin, and adenosylcobalamin. In another highly preferred embodiment, said non-proteinaceous compound is a mixture of cobalamins and/or analogues thereof.

In another preferred embodiment, said non-proteinaceous compound is a hormone, such as a steroid hormone, e.g. testosterone or cortisol. In yet another preferred embodiment, said non-proteinaceous compound is a drug (i.e. a medicament), such as methotrexate, kinidin or an antimicrobial compound, such as penicillin. In a yet further preferred embodiment, said non-proteinaceous compound is manganese.

In further embodiments, said one or more carrier proteins is/are (a) protein(s) pre-sent in blood, the cerebrospinal fluid or other body fluids. In a further preferred embodiment, said one or more carrier proteins is/are (a) protein(s) capable of binding cobalamin, more preferably transcobalamin or haptocorrin. In another more preferred embodiment, said one or more carrier proteins is transcobalamin and haptocorrin, i.e. both complexes of non-proteinaceous compounds with transcobalamin and complexes of non-proteinaceous compounds with haptocorrin are separated from the unbound non-proteinaceous compound in step i).

In a highly preferred embodiment, and said one or more carrier proteins is a cobalamin-binding protein, such as transcobalamin and/or haptocorrin, and said non-proteinaceous compound is cobalamin, a subspecies of cobalamin, an analogue of cobalamin or a mixture of cobalamins and analogues thereof.

In another preferred embodiment, said non-proteinaceous compound binds to said one or more carrier proteins with a dissociation constant below 1 micromolar, preferably below 1 nanomolar, more preferably below 1 picomolar.

In preferred embodiments of the above quantification method, the sample is a biological sample. In a more preferred embodiment, the biological sample is a blood sample, a cerebrospinal fluid sample or a tissue sample. Other preferred types of samples include waste water samples, environmental samples, food samples and feed samples. It may be advantageous to dissolve, suspend and/or homogenise some types of samples prior to step i) of the method of the invention. In a highly preferred embodiment, the sample is a waste water sample or an environmental sample and the non-proteinaceous compound detected is a hormone, such as a steroid hormone. The presence of hormones in waste water is a serious threat to the quality of ground water.

In principle, step i) of the method of the invention is optional, and omitting it modifies the method to a method for quantifying the total level (bound to protein+unbound) of non-proteinaceous compound in the sample, preferably cobalamin, a subspecies of cobalamin, an analogue of cobalamin, or a mixture of cobalamins and analogues thereof, most preferably with transcobalamin and/or haptocorrin as carrier protein.

When the one or more carrier proteins include a glycoprotein, an at least partial deglycosylation of said one or more carrier proteins may be performed prior to step i) or step ii). This can improve accessibility of the protein for the enzyme used in step ii). Said deglycosylation may be performed using any deglycosylating enzyme known in the art, including neuraminidase (E.C. 3.5.1.18) and/or peptide N-glycosidase F (E.C. 3.5.1.52).

Step i) of the method of the invention may comprise any type of separation or purification method known in the art, including chromatographic methods such as e.g. HPLC, gel filtration, etc. Examples of suitable methods are given in Current Protocols in Protein Sciences, 2005, Ed. Coligan et al. (John Wiley & Sons). In preferred embodiments, step i) of the above method comprises precipitating said complex of non-proteinaceous compound and carrier protein. Said precipitation is preferably carried out using antibodies against said one or more carrier proteins. The separation in step i) can e.g. be carried out using a solid phase on which antibodies against said one or more carrier proteins have been immobilised.

Preferably, said one or more enzymes used in step ii) comprise at least one enzyme capable of hydrolysing at least one chemical bond in said one or more carrier protein or, if present, its carbohydrate side-chain. In further preferred embodiments, the one or more enzymes used in step ii) is/are (a) deglycosylating enzyme(s) and/or (a) proteolytic enzyme(s). If the non-proteinaceous compound is bound to the polypeptide chain of the one or more carrier proteins, then a proteolytic enzyme will normally be used to release the non-proteinaceous compound. If the non-proteinaceous compound is bound to a glycosylation carried on the one or more carrier proteins, then a deglycosylating enzyme may be used to release the non-proteinaceous compound. In some embodiments, a combination of a proteolytic enzyme and a deglycosylating enzyme will be used.

More preferably, said proteolytic enzyme is an endopeptidase. Even more preferably, said proteolytic enzyme is a serine protease, most preferably proteinase K (E.C. 3.4.21.64) or a subtilisin (E.C. 3.4.21.62), such as subtilisin Carlsberg. Said deglycosylating enzyme(s) is/are preferably neuraminidase (E.C. 3.5.1.18) and/or peptide N-glycosidase F (E.C. 3.5.1.52). In other more preferred embodiments, the proteolytic enzyme is an aspartic protease, such as pepsin, or thermolysin.

It may be of interest to quantify only a specific fraction or subspecies of the non-proteinaceous compound molecule released in step ii), for example a fraction or subspecies that is biologically active in humans or can be converted to an active form. This may be done by carrying out the quantification step iii) using a method that only detects the fraction or subspecies of interest or discriminates the fraction or subspecies of interest from other fractions, e.g. a method that discriminates between any one or more of: cyanocobalamin, hydroxycobalamin, methylcobalamin, and adenosylcobalamin; or a method that discriminates between cobalamin and analogues of cobalamin.

Alternatively, in some embodiments of the method, an intermediate step is carried out after step ii) and prior to step iii), said intermediate step comprising isolation of one or more different fractions of said non-proteinaceous compound. In a preferred embodiment, when the non-proteinaceous compound is cobalamin or a mixture of cobalamin and analogues thereof, said intermediate step comprises isolation of cyanocobalamin, and step iii) is carried out on the resulting isolated cyanocobalamin. Preferably, said isolation of cyanocobalamin comprises the use of HPLC. In another preferred embodiment, said intermediate step comprises separation of cobalamins from analogues of cobalamin, such as analogues of cobalamin that bind transcobalamin and/or haptocorrin. In a similar preferred embodiment, said intermediate step comprises separation of forms of cobalamin that are biologically active in humans from analogues that are not biologically active. Accordingly, the method of the invention may be used to analyse whether or not the molecules that are bound to transcobalamin and/or haptocorrin in the blood of an individual are biologically active forms of cobalamin. This may assist in obtaining a more refined diagnosed of a patients suffering from or suspected to suffer from cobalamin related diseases.

Detection and quantification of the released non-proteinaceous compound in step iii) can be performed in many ways, e.g. using spectrophotometric, densitometric, chromatographic or immunochemical techniques, etc. Several methods for the detection of unbound (released) cobalamin are known in the art, see, for example, the prior art references given herein. In some embodiments, step iii) comprises a step of adding a catching protein that binds the unbound non-proteinaceous compound thus facilitating detection, e.g. by performing a competition experiment with labelled cobalamin. When the catching protein is added, this should occur under conditions wherein said catching protein is not degraded to an extend that it looses its ability to bind the non-proteinaceous compound. This can in some embodiments be achieved by adding an inhibitor of the enzyme used in step ii) to release the non-proteinaceous compound, such as a protease inhibitor, e.g. phenylmethanesulfonyl fluoride. Step iii) will often further comprise quantitative determination of the complex formed between the non-proteinaceous compound and the catching protein or quantitative determination of the proportion of the catching protein that is not in complex with the non-proteinaceous compound. Preferably, an antibody against said complex or catching protein is used herein.

In preferred embodiments, the non-proteinaceous compound to be detected is cobalamin, a subspecies of cobalamin, an analogue of cobalamin or a mixture of cobalamins and analogues thereof, and said catching protein is selected from the group consisting of intrinsic factor, transcobalamin and haptocorrin.

The enzymatic reaction in step ii) is preferably completed within 60 minutes, e.g. within 30 minutes, such as within 20 minutes, e.g. within 15 minutes, such as within 10 minutes, e.g. within 5 minutes, such as within 3 minutes, e.g. within 2 minutes, such as within 1 minutes, e.g. within 30 seconds, such as within 10 seconds. The rapid action of the enzyme allows the use of the method in high-throughput systems.

In a preferred embodiment, the above methods of the invention comprise an initial step of providing a sample. In a more preferred embodiment, this step of providing a sample does not include a step which is practised on a human or animal body.

Methods for Determining Absorption

In a further main aspect, the invention relates to a method for determining uptake or absorption of cobalamin in an individual comprising the steps of:
  i) providing two blood samples from said individual, wherein the first sample was taken before ingestion by said individual of non-radioactive cobalamin or an analogue thereof, together with cobalamin binding protein or without a cobalamin binding protein, and the second sample was taken after said ingestion,
  ii) determining the concentration of cobalamin in said samples using any of the quantification methods defined herein above, and
  iii) determining, on the basis of comparison of said concentrations in said two samples, whether said cobalamin or analogue thereof has been absorbed in the blood stream.

The above method of the invention is an improved form of the Schilling test and has the advantage of avoiding ingestion of radioactive material. In a preferred embodiment of the above method of absorption, said cobalamin is cyanocobalamin and the concentration of cyanocobalamin is determined using the quantification methods defined herein. The optional cobalamin binding protein of step i) is preferably intrinsic factor.

The cobalamin used for oral administration is a non-radioactive form. The purpose of the administration of cobalamin may be therapeutic or non-therapeutic. One, two, three or more doses can be taken at regular intervals, for example every six hours. Repeated ingestion of cobalamin may increase the concentration of holo-TC and possibly also holo-HC in the blood if absorption of cobalamin occurs. Administration of several times the recommended daily dose of cobalamin will result in a significant increase of the holo-TC concentration in the blood, if the absorption system works well. Use of small doses of cobalamin (less than 0.5 nanomole), as in the Schilling test, will not give a significant increase in holo-TC in the blood. Preferably, the dose is chosen such that passive absorption (i.e. absorption not mediated by intrinsic factor) is minimised. Thus, preferably, the total ingested dose of cobalamin is between 0.5 and 500 nanomole, more preferably between 1 and 250 nanomole, even more preferably between 2 and 100 nanomole, most preferably between 5 and 50 nanomole. In a particularly preferred embodiment, three doses of cobalamin are ingested, each being between 5 and 15 nanomoles.

Blood samples taken some hours e.g. the next morning after ingestion of cobalamin favours a maximal change in holo-TC concentration in the blood if cobalamin can be absorbed from the intestine and transferred to TC in the blood. In one preferred embodiment the concentration of holo-TC and/or holo-HC and/or total-TC and/or total-HC in the blood is measured less than 48 hours, more preferably 8-16 hours, after the last ingestion of cobalamin. If two or more versions of the test are to be carried out in the same patient (e.g. following ingestion of cobalamin alone, ingestion of cobalamin with haptocorrin and/or ingestion of cobalamin with intrinsic factor) then in the second test, the initial concentration of holo-TC and/or holo-HC and/or total-TC and/or total-HC in the blood more than 48 hours, preferably 5-10 days after the last administration of cobalamin, is measured.

The cobalamin-binding proteins are proteins capable of binding cobalamin or analogues thereof. The cobalamin binding proteins used in this invention are transcobalamin, intrinsic factor and haptocorrin or functional equivalents of any one of these proteins. The cobalamin binding proteins used for ingestion and analysis of plasma cobalamin concentrations may be native e.g. from human, pig or recombinant cobalamin binding proteins produced in e.g. yeast, plants, plant cells, insect cells, mammalian cells. The cobalamin binding proteins are preferably recombinant human proteins produced by yeast or transgenic plants since this will eliminate the risk of transferring mammalian pathogens from sources of intrinsic factor and haptocorrin that contain other mammalian material.

The cobalamin, intrinsic factor and haptocorrin are normally suitable or adapted for oral administration. They may be presented as discrete units such as capsules or tablets; powders or granules; solutions or suspensions in aqueous or non-aqueous liquids; edible foams or whips; or oil-in-water liquid emulsions or water-in-oil liquid emulsions.

Further guidance for carrying out the absorption assay be found in WO 2004/081577, incorporated herein by reference.

In a preferred embodiment, the above method for determining adsorption comprises an initial step of providing a sample. In a more preferred embodiment, this step of providing a sample does not include a step which is practised on a human or animal body.

Methods of Quantifying Glycoproteins

In a further main aspect, the invention relates to a method for quantifying a glycoprotein in a sample comprising the steps of:
  i) treating a sample with one or more deglycosylating enzymes; and
  ii) quantifying said glycoprotein.

In a preferred embodiment, said glycoprotein is a heterogeneously glycosylated protein, i.e. a glycoprotein that contains acceptor sites for glycosylation that are not always utilised, such as a glycoprotein containing one or more N—X—S acceptor sites for glycosylation, or a glycoprotein containing heterogeneous carbohydrate structures, e.g. a glycoprotein containing N or O-linked glycosylations produced in human cells. In another preferred embodiment, said glycoprotein is a heavily glycosylated protein, e.g. a glycoprotein wherein the glycosylations make up more than 5%, such as more than 10%, e.g. more than 20%, e.g. more than 50%, such as more than 80%, e.g. more than 90%, such as more than 95% of the molecular weight of the glycoprotein. In a further preferred embodiment, said glycoprotein exhibits significant variation between individuals, e.g. significant variation between different patients.

In an even more preferred embodiment, said glycoprotein is a cobalamin-binding protein, preferably haptocorrin or intrinsic factor.

In preferred embodiments, a pre-treatment step is performed prior to step i) in order to increase or decrease the concentration of the glycoprotein, or to remove sub-stance that might interfere with the treatment in step i).

In some embodiments, a subgroup of said cobalamin-binding protein is removed prior to step i) or between step i) and step ii). For instance, if the cobalamin-binding protein is haptocorrin, apo-haptocorrin can be removed, e.g. by adsorption to vitamin-B12 beads, where after the remaining holo-haptocorrin is quantified in step ii).

The quantification method defined above can e.g. be used for the quantification of total haptocorrin or holohaptocorrin for the evaluation of cobalamin stores or for the evaluation of tumour burden in tumours that synthesise haptocorrin, such as Chronic myeloid leukaemia or solid tumours, e.g. liver tumours.

The sample in the above method is preferably a biological sample. In a more preferred embodiment, said biological sample is a blood sample. In another more preferred embodiment said biological sample is a tissue sample. In a highly preferred embodiment, said biological sample is a sample from a cancer patient.

The one or more deglycosylating enzymes used in step i) can be any enzymes that at least partially remove glycosylation. The deglycosylating enzyme is preferably selected from the group consisting of neuraminidase (E.C. 3.5.1.18), peptide N-glycosidase F (E.C. 3.5.1.52), endoglycosidase H, peptide N-glycosidase A, O-glycosidase, and endoglycosidase F. Most preferred is treatment with both neuraminidase (E.C. 3.5.1.18) and peptide N-glycosidase F (E.C. 3.5.1.52). Neuraminidase cleaves terminal sialic acid residues and peptide N-glycosidase F (PNGase) cleaves virtually all N-linked oligosaccharides from glycoproteins.

The deglycosylation can be complete but does not have to be complete. In some cases, partial deglycosylation is sufficient to improve detection. Thus, it is not required that the entire carbohydrate side-chain attached to the polypeptide chain is removed, treatment with deglycosylating enzymes that leave e.g. a core of the glycosylation behind can be used as well.

In preferred embodiment, step ii) comprises the use of an indicator moiety, such as an antibody, that binds to the glycoprotein. The indicator moieties are ones which bind to the target protein in such way or at such (a) position(s) that the binding to the target protein is reduced or affected by the presence of glycosylation. Thus, the quantification of step ii) is carried out by a method that is negatively affected by carbohydrates present on the protein.

A preferred type of indicator moiety is an antibody against said glycoprotein, preferably an antibody against a peptide epitope of said glycoprotein. Said antibody may be monoclonal or polyclonal. A preferred method of quantification is ELISA.

In a preferred embodiment, the above methods of the invention comprise an initial step of providing a sample. In a more preferred embodiment, this step of providing a sample does not include a step which is practised on a human or animal body.

EXAMPLES

Example 1

Release of Cyanocobalamin from Transcobalamin Using Proteases

Materials

The proteases used were: Chymotrypsin from bovine pancreas (EC 3.4.21.1), proteinase K from *Tritrachium album* (EC 3.4.21.64) (Sigma Aldrich), subtilisin Carlsberg from *Bacillus licheniformis* (EC 3.4.21.62) (Sigma Aldrich), and thermolysin from *Bacillus thermoproteolyticus* (EC 3.4.24.27).

Serum was from human donors and was stored at $-20°$ C., the sera were obtained from the Department of Clinical Biochemistry, Aarhus University Hospital, Denmark. Tracer solution: $^{57}$Co cyanocobalamin (Cat. No. 06B-430000, ICN) 2.6 nM, cyanocobalamin 7.4 nM, $NaCl_2$ 0.36%, Sodium azide 0.02%, Human albumin $34 \times 10^{-5}$%. Cyanocobalamin solution: 218 nM cyanocobalamin (Sigma-Aldrich). Capturing reagent: coated magnetic microspheres with murine monoclonal antibodies to human TC (AXIS-Shield ASA; Norway). Washing buffer and extractant from HoloTC AXIS RIA kit (AXIS-Shield ASA, Norway).

Magnetic rack XS-20 (Abgene), vortex mixer (REAX 2000 Heidolph), coulter mixer (Coulter Electronics Limited), thermo stated shaking water bath (Heto Lab Equipment, Denmark), centrifuge (4K15 Sigma Laboratory Centrifuges), Gamma counter (1470 Wizard Wallac).

Methods and Results

25 µl tracer solution and 2.5 µl cyanocobalamin solution were added to 400 µl human donor serum. Tris-HCl 0.1 M pH 7.4 was run as a control. After addition of 50 µl capturing reagent, the samples were incubated on a coulter mixer for 1 hour at room temperature. The samples were placed in a magnetic rack for 3 minutes for separation of the capturing reagent. Subsequently, the rack was inverted and incubated for another 3 minutes. The supernatant was discarded and 500 µl of washing buffer was added. The samples were vortexed and placed in the magnetic rack for 3 minutes. Subsequently, the rack was inverted again and the samples were incubated for another 3 minutes. After separation, the washing buffer was discarded and 50 U of subtilisin Carlsberg, in 200 µl Tris-HCl 0.1 M pH 7.4 5 mM $Ca^{2+}$, was added. After incubation for 15 minutes at 50° C. in a shaking water bath, the samples were put on a magnetic rack for 3 minutes for separation of the capturing reagent. The rack was inverted and incubated for another 3 minutes. The supernatant was discarded and the pellet was counted for 5 minutes on a gamma counter.

Similar experiments were performed with proteinase K (50 U) in Tris-HCl 0.1 M pH 7.4 5 mM $Ca^{2+}$ incubated at 37° C., thermolysin (50 U) in Tris-HCl 0.1 M pH 7.4 5 mM $Ca^{2+}$ 5 mM $Zn^{2+}$, and chymotrypsin (50 U) in Tris-HCl 0.1 M pH 7.4 incubated for 45 min. at 37° C. Extractant (25 µl), incubated at room temperature for 15 min., was used for comparison.

Figure 1:
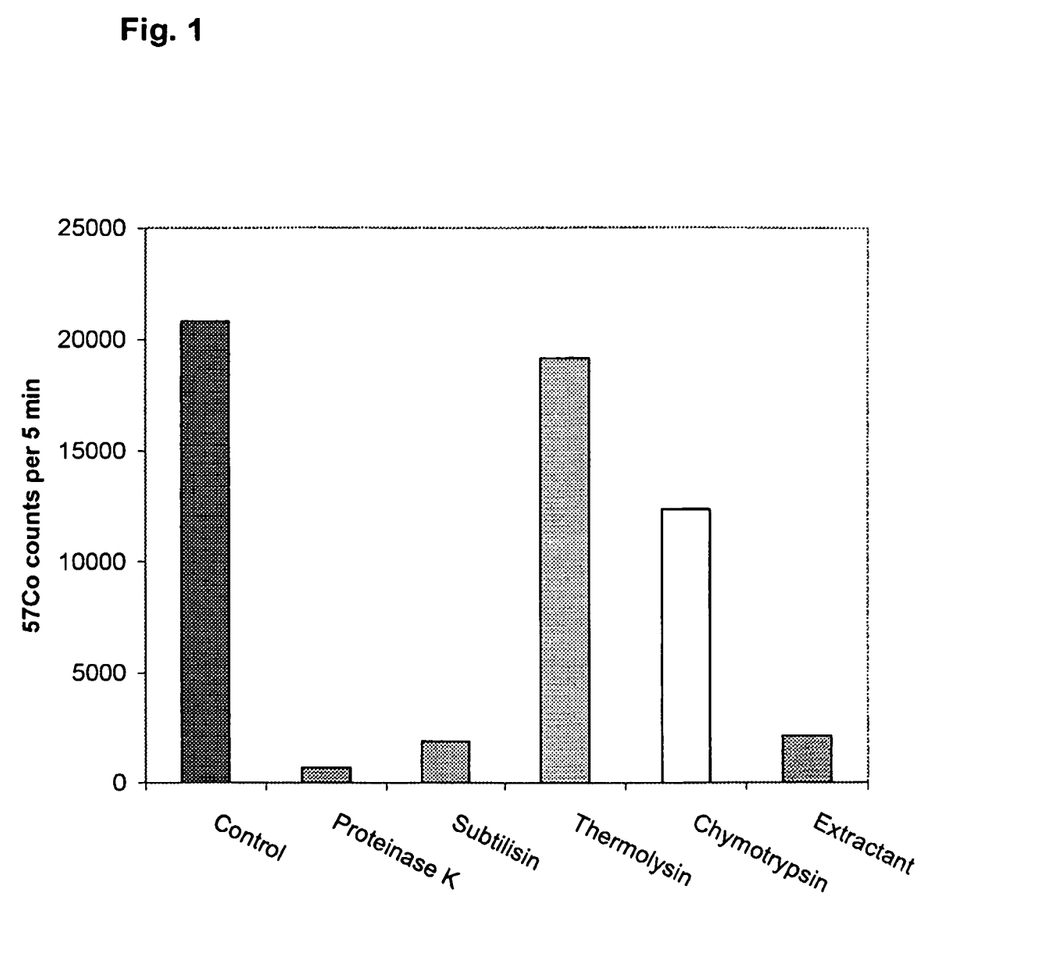
FIG. 1. TC-bound 57Co cobalamin after extraction with 50 U proteinase K, subtilisin, thermolysin and chymotrypsin. Extractant from HoloTC AXIS RIA kit (AXIS-Shield ASA) was used for comparison. Incubation with proteinase K, subtilisin, thermolysin and extractant was performed for 15 minutes and chymotrypsin for 45 minutes.

The results of the experiments are shown in FIG. 1. All proteases decrease the number of counts remaining in the sample, indicating that they are capable of releasing cyanocobalamin from its complex with transcobalamin. Proteinase K and subtilisin Carlsberg were the most effective.

Figure 2:
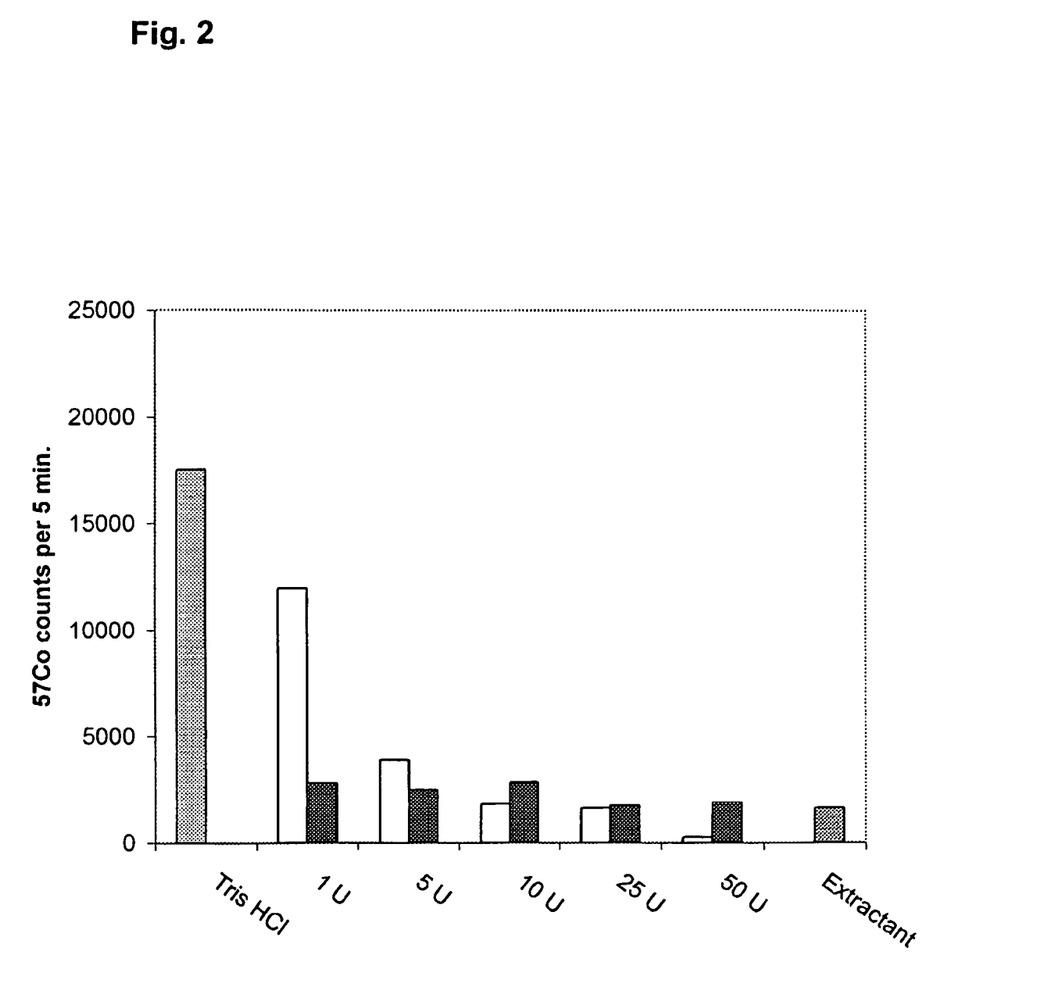
FIG. 2. TC-bound 57Co cobalamin after extraction with 1, 5, 10, 25 and 50 U of proteinase K or subtilisin. Extractant from HoloTC AXIS RIA kit (AXIS-Shield ASA) was used for comparison.

The optimal concentration for extraction of cobalamin from TC with proteinase K and subtilisin was determined in the same experimental design using concentrations ranging from 1 to 50 U and 15 min incubation time. Extractant (15 µl) was used as comparison. Incubation was performed at room temperature. The results of these experiments are shown in FIG. 2.

Figure 3:
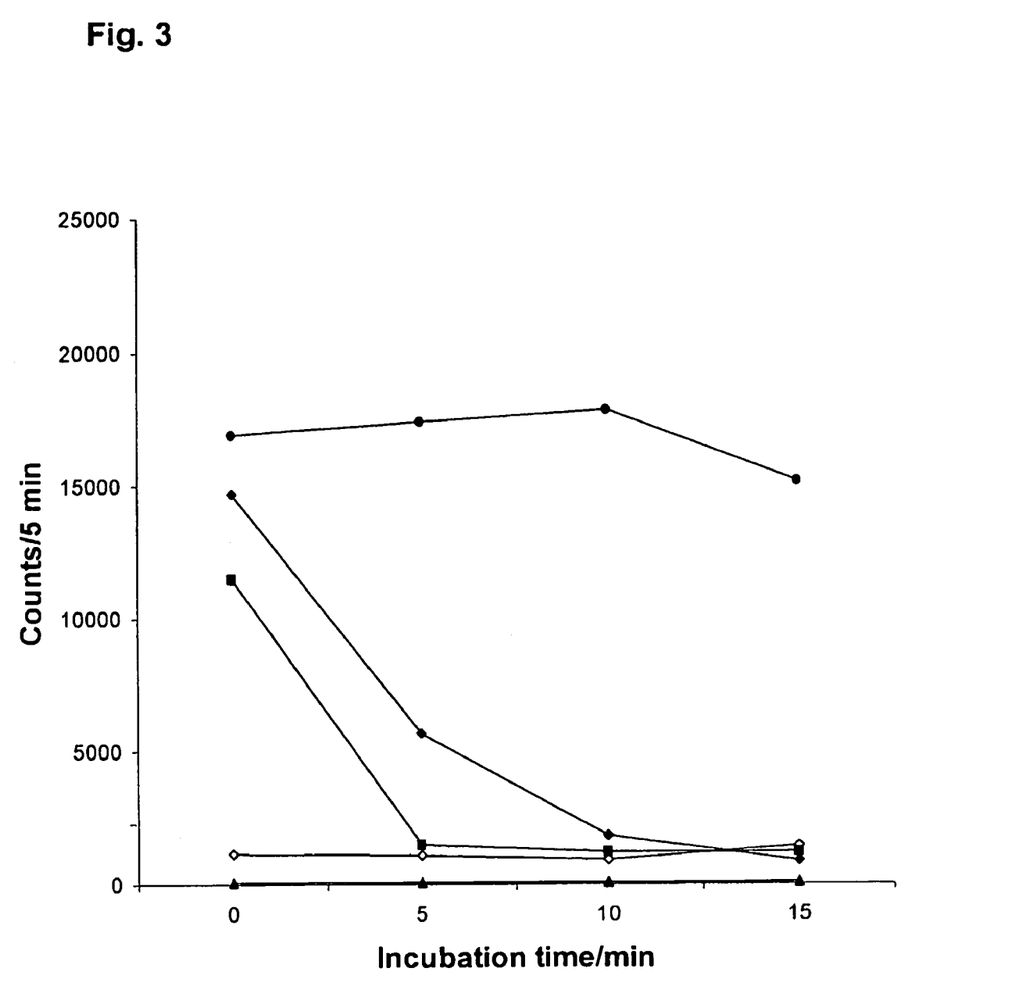
FIG. 3. TC-bound 57Co cobalamin after extraction with proteinase K or subtilisin, respectively, for 0, 5, 10 and 15 min. Extractant from HoloTC AXIS RIA kit (AXIS-Shield ASA) was used for comparison.

The extraction of cobalamin from TC was followed over time using proteinase K (50 U) and subtilisin (25 U) in the same experimental design. Incubation was stopped after 0, 5, 10 and 15 min. Results are shown in FIG. 3.

Example 2

Glycosylation Independent Measurement of Haptocorrin

Materials and Methods

The deglycosylating enzymes used were neuraminidase (E.C. 3.5.1.18, Sigma Aldrich) from *Clostridium Perfringens* cleaving terminal sialic acid residues (α-2-3 linked residues are most efficiently cleaved) and peptide N-glycosidase F (PNGase) (E.C. 3.5.1.52, New England BioLabs) from *Flavobacterium Meningoseptum* cleaving virtually all N-linked oligosaccharides from glycoproteins.

Deglycosylation. EDTA plasma samples or controls (50 µL) were mixed with 50 µL sodium phosphate buffer 0.1 mol/L pH 7.4 containing neuraminidase 0.08 U/ml and PNGase 2000 U/ml and incubated at 37° C. for 16 hours prior to analysis.

Antibodies. Anti haptocorrin was produced by DakoCytomation A/S, Denmark by immunising rabbits with 200 µg pure haptocorrin produced as previously described (12) and deglycosylated as described above. The gamma globulin fraction was pre-pared (13) from serum obtained after 7 immunisations.

ELISA. The principle of the ELISA assay used was an immobilised capture antibody (0.1 ug gamma globulin/well, rabbit nr F7773) catching the analyte and a biotinylated detection antibody (gamma globulin 3 ug/L, rabbit nr 7772) visualised by avidin/Horse Radish Peroxidase (HRP). Colour development by addition of 3,3',5,5'-tetramethyl-benzidin was proportional to the concentration of analyte. The assay procedure was as previously described for transcobalamin (14, 15). In brief, calibrator, sample or control (100 µL, final dilution 1:30) was incubated for 1 hour at room temperature prior to washing and incubation for 30 min with the biotinylated detection antibody. The attached biotinylated antibody was detected employing avidin/HRP and colour development was determined by measuring the absorbance at 420 nm and correcting for the absorbance at 620 nm. The calibrator employed was deglycosylated pure human haptocorrin. All samples were run in true duplicates, where deglycosylation was performed on two independent samples.

Samples. EDTA plasma samples were obtained from healthy donors (women≦50 years, n=36; women>50 years, n=35; men≦50 years, n=37 and men>50 years, n=40). The low control was prepared from a pool of plasma drawn from vegans having a low content of haptocorrin, the intermediate and high controls were plasma drawn from healthy donors spiked with plasma from a patient with a more than 10000 fold increase in haptocorrin content (16). Samples containing IF and TC were prepared by dissolving pure TC and IF in phosphate buffer 0.1 M containing albumin 0.1%.

For statistical analysis linear regression and unpaired t-test was employed using GraphPad Prism 4.0.

The sensitivity of the ELISA was 1.9 pmol/L, calculated as described below and a measurement range from 1.6-100 pmol/L. The lower limit of detection and quantification was estimated from the signal of the lowest calibrator corrected for the signal of the zero calibrator (LLD=mean+3× SD=0.032; n=22 and LLQ=mean+10×SD=0.06; n=22). This resulted in a LLD in the range of 1.9 µmol/L and a LLQ around 4.1 µmol/L. The sensitivity compares with the previously described assays for direct haptocorrin measurement (17).

No cross-reactivity was observed towards other cobalamin binding proteins for concentrations in the assay mixture of 60 nmol/L for intrinsic factor and 100 nmol/L for transcobalamin. Despite some comparability in the protein structure of the three cobalamin binding proteins (17) our ELISA was specific for haptocorrin.

The assay imprecision was determined by analysing the low, an intermediate and a high plasma control in quintuple in four different assays performed on different days. Each pre-treated plasma control was run in duplicate on the ELISA plate to determine the total imprecision on the ELISA assay. The assay performed equally well on the three levels tested (250, 516 and 835 pmol/L). The total imprecision on the assay including pre-treatment was 4.5-4.9% where the ELISA part accounted for ~3%. The intra-assay imprecision was the major contributor to the imprecision. The imprecision was lower than obtained with previous published assays (9, 11).

Figure 4:
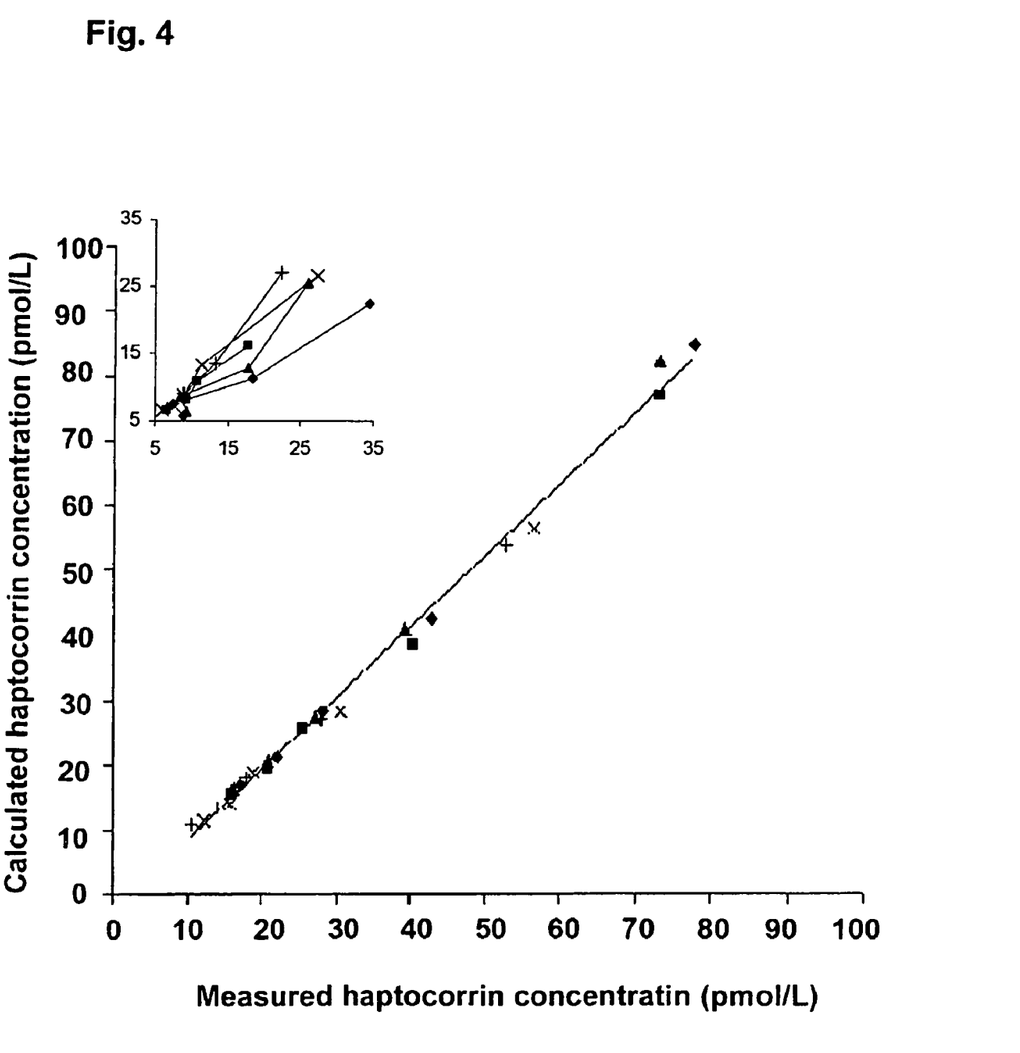
FIG. 4. Measured versus calculated haptocorrin. The calculation of haptocorrin was based on the measured result from the 10-fold dilution. A: Neuraminidase- and PNGase-treated plasma samples. Inserted figure: untreated plasma samples. ■ plasma 1; ◆ plasma 2; ▲ plasma 3; x plasma 4 and + plasma 5.

To test the linearity of the ELISA assay we used 5 plasma samples that had been deglycosylated or not. The samples were diluted with phosphate buffer 0.1 M containing albumin 0.1% to give a final dilution of 5-, 10-, 15- or 20-fold, respectively (FIG. 4). The expected concentrations to be detected in samples diluted 5-, 15-, or 20-fold was calculated based on the concentration obtained for samples diluted 10 fold. While untreated samples showed a poor linearity the deglycosylated samples showed an excellent linearity. The concentration of haptocorrin measured in the deglycosylated samples was higher than in the untreated samples (FIG. 4). An explanation for this could be a sub-class of unrecognised haptocorrin of varying concentration in the different plasma samples resulting in non-parallel dilution curves and less detected haptocorrin.

Figure 5:
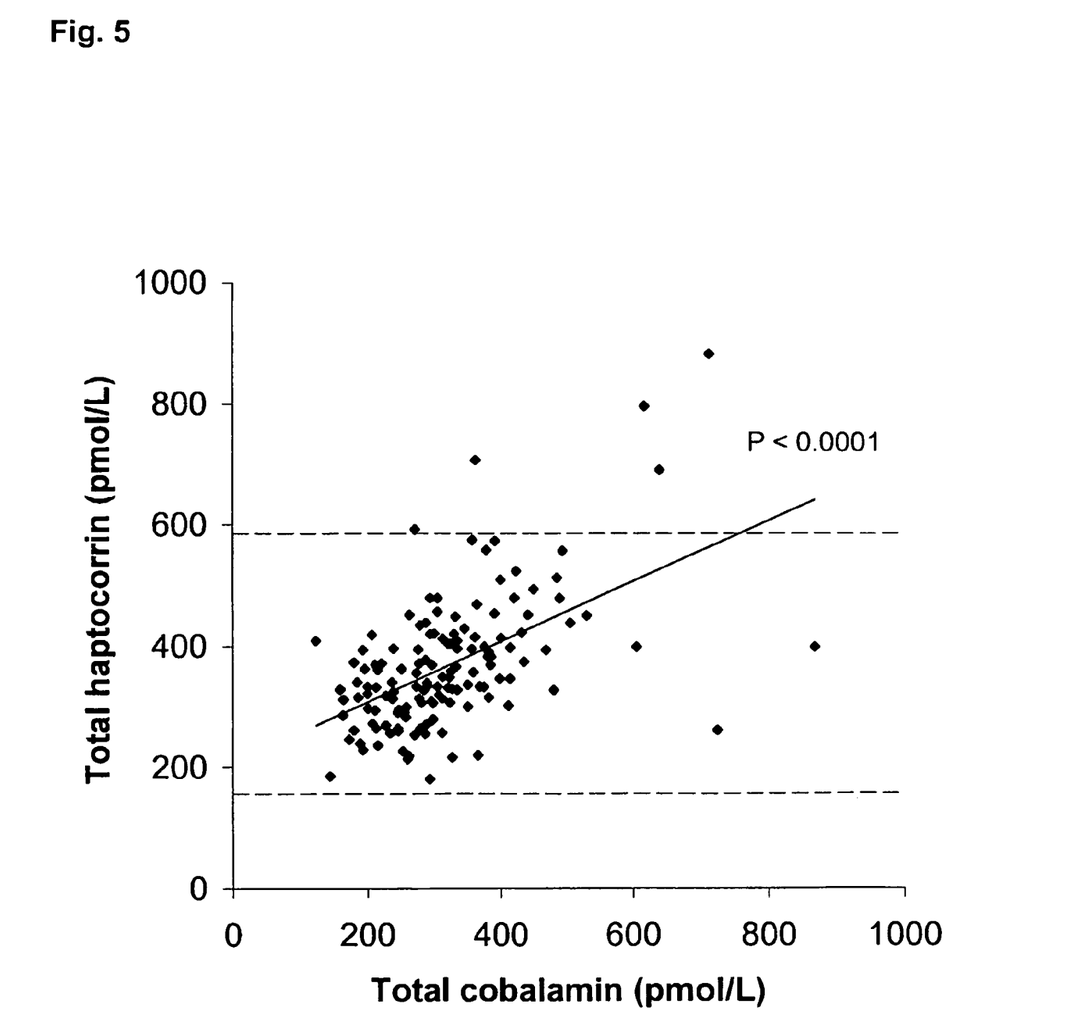
FIG. 5. Plasma cobalamin versus plasma haptocorrin measured on 148 donors. ◆ indicates the mean of double estimates of haptocorrin for each individual. Cobalamin was measured in single estimate. The broken line indicates the 95% interval.

The reference interval for haptocorrin was determined on plasma from 148 healthy donors. The samples were pretreated in duplicate and assayed in the ELISA assay. The 95% interval was 160-590 pmol/L (mean=370 pmol/L). No significant sex or age (individuals≦50 and >50 years were compared) related difference was shown (unpaired t-test). Interestingly we found a strong correlation between the level of plasma cobalamin and haptocorrin (FIG. 5). Without being bound by any specific theory, the result may support the view that persons with low levels of cobalamin are heterozygous for lack of haptocorrin (8), but it may also indicate that the concentration of haptocorrin is influenced by the cobalamin status.

REFERENCES

1. Nexø E, Olesen H, Christensen J M, Thomsen J, Kristiansen K. Characterisation of a cobalamin-binding plasma protein from a patient with hepatoma. Scand J Clin Lab Invest 1975; 35:683-90.
2. Burger R L, Mehlman C S, Allen R H. Human plasma R-type cobalamin-binding proteins. I. Isolation and characterisation of transcobalamin I, transcobalamin III and the normal granulocyte vitamin B12-binding protein. J Biol Chem 1975; 250:7700-6.

3. Stenman U H. Characterization of R-type vitamin B12-binding proteins by isoelectric focusing. II. Comparison of cobalophilin (r proteins) from different sources. Scand J Clin Lab Invest 1975; 35:147-55.
4. Nexø E. Transcobalamin I and other human R-binders: Purification, structural and physiological studies. FADL's forlag, Copenhagen 1978
5. Yang S Y, Coleman P S, Dupont B. The biochemical and genetic basis for the microheterogeneity of human R-type vitamin B12 binding proteins. Blood 1982; 59:747-55.
6. Carmel R. Vitamin B12-binding proteins in serum and plasma in various disorders. Effect of anticoagulants. Am J Clin Pathol 1978; 69:319-25.
7. Gimsing P, Hippe E. Increased concentration of transcobalamin I in a patient with metastatic carcinoma of the breast. Scand J Haematol 1978; 21:243-9.
8. Carmel R. Mild transcobalamin I (haptocorrin) deficiency and low serum cobalamin concentrations. Clin Chem. 2000; 49:1367-74.
9. Morelli T A, Begley J A, Hall C A. A radioimmunoassay for the R-type binders of cobalamin. Clin Chim Acta 1977; 77:365-72.
10. Carmel R. R-binder deficiency. A clinically benign cause of cobalamin pseudodeficiency. JAMA 1983; 250:1886-90.
11. Carmel R, Brar S, Frouhar Z. Plasma total transcobalamin I. Ethnic/racial patterns and comparison with lactoferrin. Am J Clin Pathol 2001; 116:576-80.
12. Nexø E. A new principle in biospecific affinity chromatography used for purification of cobalamin binding proteins. Biochim Biophys Acta 1975; 379:189-92
13. Petersen E A, Sober H A. In: Putman F W ed. The plasma proteins. NY: Academic Press 1960:105.
14. Nexø E, Christensen A-L, Petersen T E. Measurement of transcobalamin by ELISA. Clin Chem 2000; 46:1643-9
15. Jorgensen P E, Vinter-Jensen L, Nexø E. An immunoassay designed to quantitate different molecular forms of rat urinary epidermal growth factor with equimolar potency: application fresh rat urine. Scand J Clin Lab Invest 1996; 56:25-36
16. Nexø E, Olesen H, Norredam K, Schwartz M. A rare case of megaloblastic anaemia caused by disturbances in the plasma cobalamin binding proteins in a patient with hepatocellular carcinoma. Scand J Haematol 1975; 14:320-7.
17. Nexø E. In: Krautler B, Arigoni, Golding B T eds. Vitamin B12 and B12-binding proteins. Wiley-VCH 1998:461-475.

The invention claimed is:

1. A method for determining absorption of cobalamin or an analogue thereof in an individual comprising the steps of:
   i) providing two blood samples from said individual, wherein
   the first sample comprises said individual's blood prior to ingestion by said individual of nonradioactive cobalamin or an analogue thereof and the second sample comprises said individual's blood after said ingestion,
   ii) determining the concentration of cobalamin or an analogue thereof in the first sample,
   iii) determining the concentration of cobalamin or an analogue thereof in the second sample by treating complexes of cobalamin or an analogue thereof bound to and one or more carrier proteins with one or more enzymes to release cobalamin or an analogue thereof from said one or more carrier proteins, and
   iv) determining, on the basis of comparison of said concentrations in said two samples, whether said cobalamin or analogue thereof has been absorbed.

2. The method of claim 1, wherein said cobalamin is cyanocobalamin.

3. The method of claim 1, further comprising said cobalamin or analogue thereof is ingested with intrinsic factor.

* * * * *